United States Patent
Mitani (10) Patent No.: US 8,821,155 B2
(45) Date of Patent: Sep. 2, 2014

(54) TRACTION DEVICE AND MAXILLARY TRACTION DEVICE

(71) Applicant: Kabushiki Kaisha RAMPA master product, Tokyo (JP)

(72) Inventor: Yasushi Mitani, Tokyo (JP)

(73) Assignee: Kabushiki Kaisha RAMPA master product, Tokyo (JP)

( * ) Notice: Subject to any disclaimer, the term of this patent is extended or adjusted under 35 U.S.C. 154(b) by 0 days.

(21) Appl. No.: 14/049,955

(22) Filed: Oct. 9, 2013

(65) Prior Publication Data

US 2014/0170584 A1   Jun. 19, 2014

Related U.S. Application Data

(63) Continuation of application No. PCT/JP2012/082675, filed on Dec. 17, 2012.

(51) Int. Cl.
*A61C 3/00* (2006.01)
*A61C 7/08* (2006.01)
*A61C 7/06* (2006.01)

(52) U.S. Cl.
CPC .... *A61C 7/06* (2013.01); *A61C 7/08* (2013.01)
USPC .......................................................... 433/5

(58) Field of Classification Search
USPC ...................................... 433/2–24
See application file for complete search history.

(56) References Cited

U.S. PATENT DOCUMENTS

| 4,167,061 | A | * | 9/1979 | Forster | 433/5 |
| 4,988,291 | A | * | 1/1991 | Grummons | 433/5 |
| 6,976,838 | B1 | | 12/2005 | Keles | |
| 7,677,886 | B2 | * | 3/2010 | Mitani | 433/5 |
| 2006/0029899 | A1 | | 2/2006 | Keles | |

FOREIGN PATENT DOCUMENTS

| JP | 2009-89928 | 4/2009 |
| WO | 2010/108218 | 9/2010 |

OTHER PUBLICATIONS

Written Opinion of the International Searching Authority for corresponding international application No. PCT/JP2012/082675, mailed Mar. 26, 2013, with English translation.

* cited by examiner

*Primary Examiner* — Heidi M Eide
*Assistant Examiner* — Matthew Saunders
(74) *Attorney, Agent, or Firm* — Myers Wolin, LLC (57) ABSTRACT

A traction device includes an engaging assembly engaging with a mouthpiece to be attached to a maxilla inside a mouth of a human body and a support assembly supporting the engaging assembly in contact with a face of the human body, wherein the engaging assembly pulls the mouthpiece in an anterior direction of the human body. The support assembly includes an upper contact body configured to be in contact with a forehead of the face and a lower contact body configured to be in contact with an area of the face below the forehead and above a mandible.

11 Claims, 11 Drawing Sheets

FIG. 1

BACKGROUND ART

TRACTION DEVICE AND MAXILLARY TRACTION DEVICE

CROSS-REFERENCE TO RELATED APPLICATION

This application is a continuation application of International Application PCT/JP2012/82675, filed on Dec. 17, 2012 and designated the U.S., the entire contents of which are incorporated herein by reference.

FIELD

The present invention relates to a traction device and a maxillary traction device.

BACKGROUND

Figure 1:
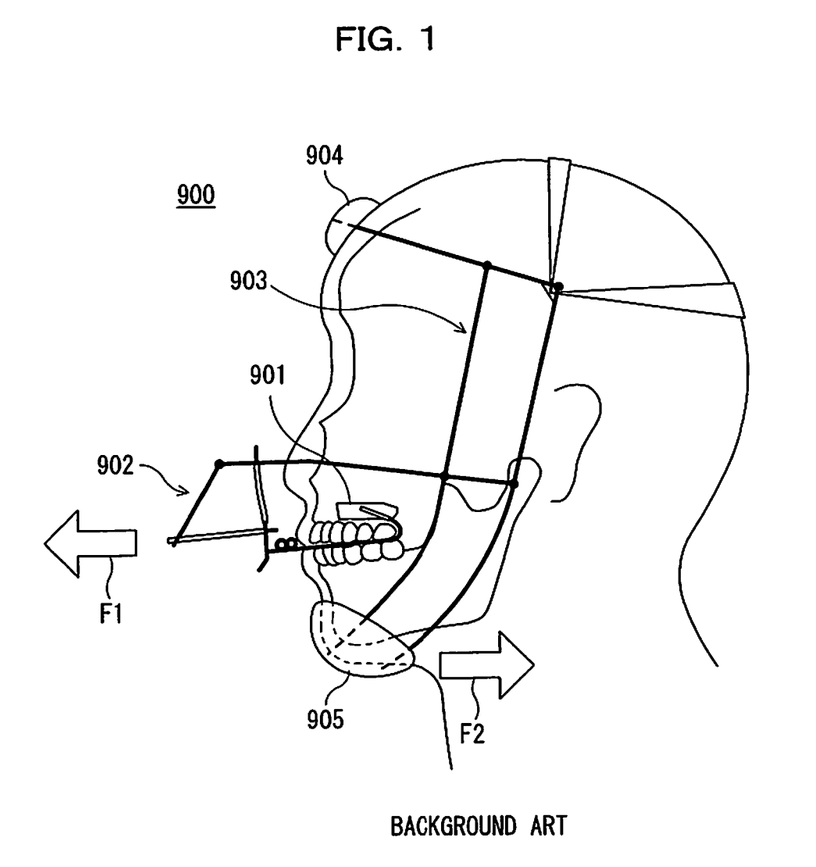
FIG. 1 is a right side view of a maxillary traction device according to the background art.

Traction devices are known that pull mouthpieces to be attached to maxillae inside mouths of human bodies. FIG. 1 illustrates a traction device 900 described in Japanese Laid-open Patent Publication No. 2009-89928 including an engaging assembly 902 that engages with a mouthpiece 901 and a support assembly 903 that supports the engaging assembly 902 in contact with a face of the human body. The engaging assembly 902 pulls the mouthpiece 901 in the anterior direction of the human body.

The support assembly 903 includes an upper contact body 904 that comes into contact with the forehead of the face and a lower contact body 905 that comes into contact with the lower edge of the mandible of the face. The upper contact body 904 and the lower contact body 905 receive a reaction force F2 generated in reaction to a force F1 from the engaging assembly 902 pulling the mouthpiece 901 through the transmission of the reaction force F2 to the face.

The lower contact body 905 of the traction device 900 described above pushes the lower edge of the mandible in the posterior direction of the human body with the reaction force F2. This may inhibit the growth or movement of the mandible in the anterior direction.

The distance between the lower edge of the mandible and the forehead and the angle to the face formed by the lower edge of the mandible and the forehead vary relatively greatly with traction of the mouthpiece 901. At least one of the upper contact body 904 and the lower contact body 905 of the traction device 900 described above may lose the contact with appropriate positions on the face in a relatively short time. In such a case, the adjustment for pulling the maxilla in an appropriate direction may be complicated.

In this way, the traction device 900 described above may require a complicated procedure for appropriate encouragement of the growth or movement of the jaw.

SUMMARY

According to an aspect of the embodiments, a traction device comprises an engaging assembly engaging with a mouthpiece to be attached to a maxilla inside a mouth of a human body and a support assembly supporting the engaging assembly in contact with a face of the human body, wherein the engaging assembly pulls the mouthpiece in an anterior direction of the human body. The support assembly comprises an upper contact body configured to be in contact with a forehead of the face and a lower contact body configured to be in contact with an area of the face below the forehead and above a mandible.

According to another aspect of the embodiments, a maxillary traction device comprises a traction device comprising a mouthpiece to be attached to a maxilla inside a mouth of a human body, an engaging assembly engaging with the mouthpiece, and a support assembly supporting the engaging assembly in contact with a face of the human body, wherein the engaging assembly pulls the mouthpiece in an anterior direction of the human body. The support assembly comprises an upper contact body configured to be in contact with a forehead of the face and a lower contact body configured to be in contact with an area of the face below the forehead and above a mandible.

The traction device according to the present invention can reduce the complexity of the procedure of appropriate encouragement of the growth or movement of the jaw.

DESCRIPTION OF EMBODIMENTS

A traction device, a maxillary traction device, and a mouthpiece according to embodiments of the present invention will now be described with reference to FIGS. 2 to 21.

First Embodiment

Configuration

With reference to FIGS. 2 to 6, a maxillary traction device 1 according to a first embodiment includes a mouthpiece 10 and a traction device 20.

Figure 2:
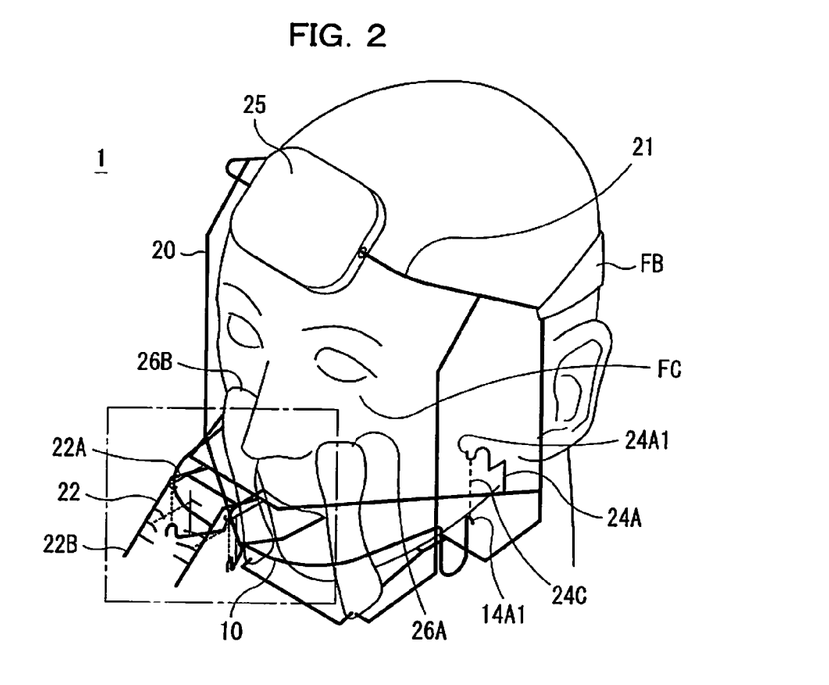
FIG. 2 is a forward perspective view of a maxillary traction device according to a first embodiment.
Figure 3:
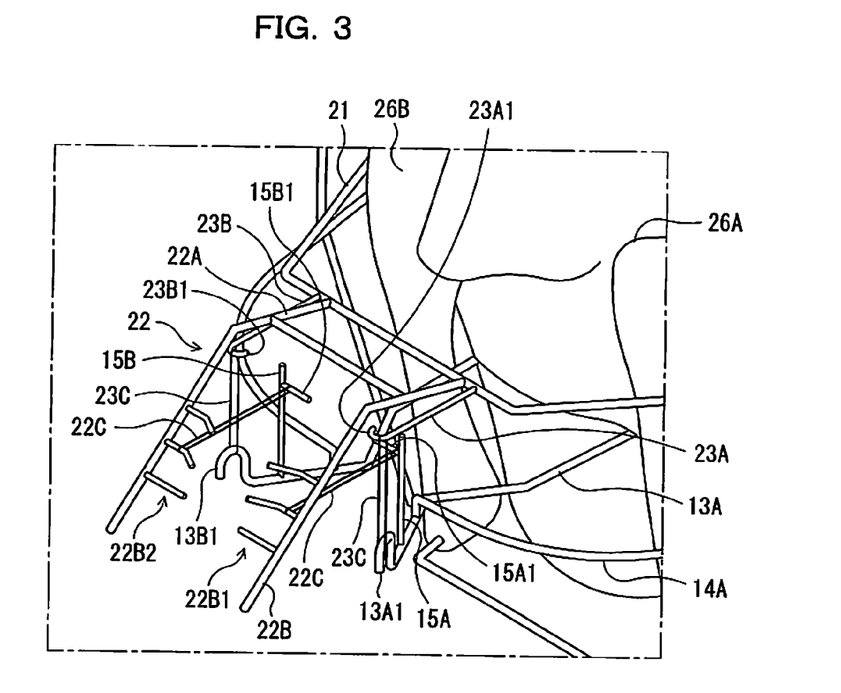
FIG. 3 is an enlarged perspective view of the area defined by the dash-dot lines in FIG. 2 of a maxillary traction device according to a first embodiment.
Figure 4:
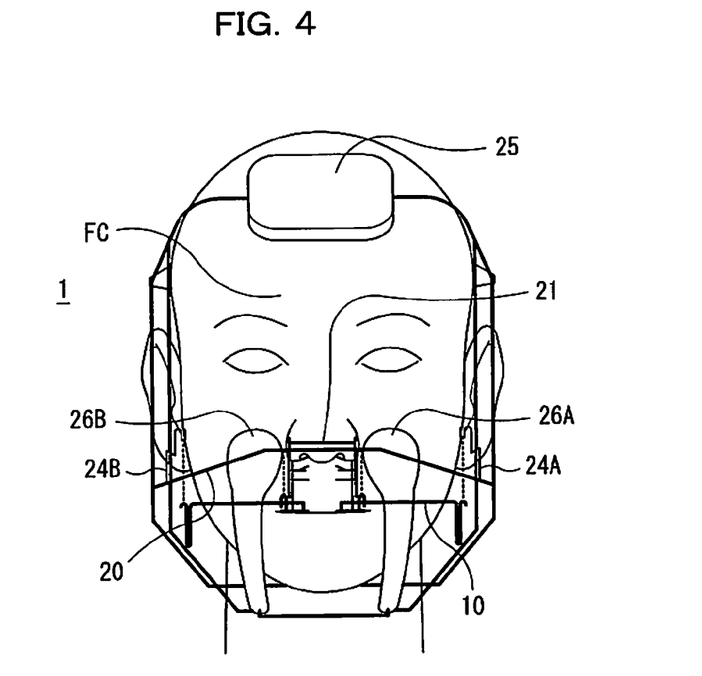
FIG. 4 is a front view of a maxillary traction device according to a first embodiment.
Figure 5:
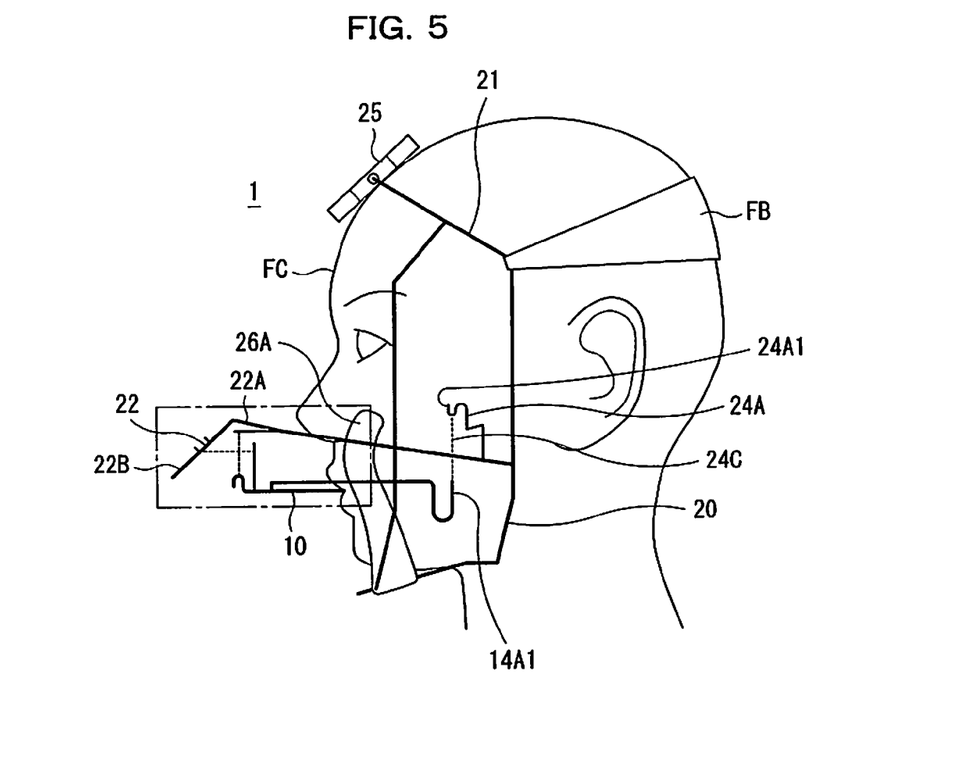
FIG. 5 is a right side view of a maxillary traction device according to a first embodiment.
Figure 6:
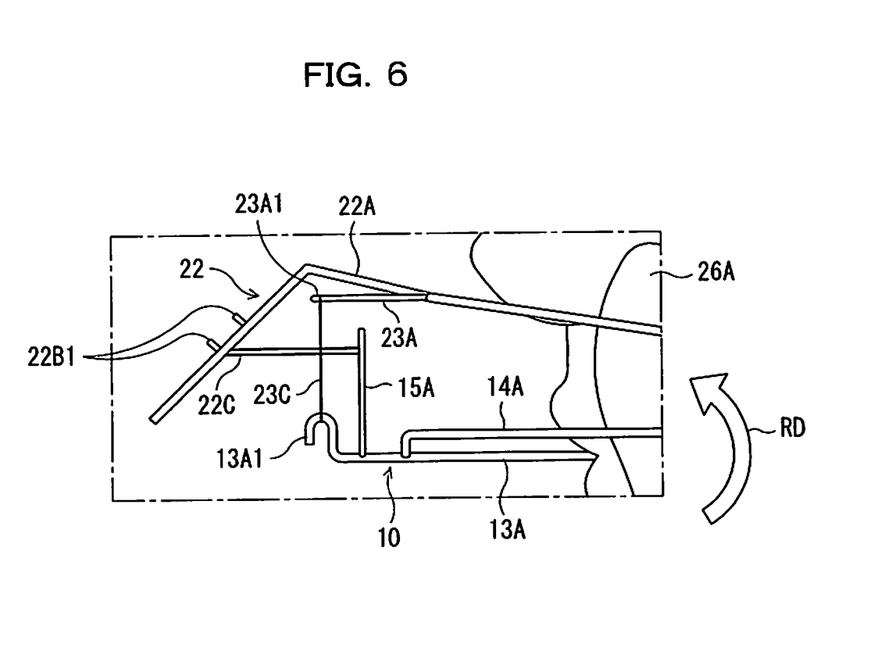
FIG. 6 is an enlarged side view of the area defined by the dash-dot lines in FIG. 5 of a maxillary traction device according to a first embodiment.

FIG. 2 is a forward perspective view of the maxillary traction device 1. FIG. 3 is an enlarged perspective view of the area defined by the dash-dot lines in FIG. 2 of the maxillary traction device 1. FIG. 4 is a front view of the maxillary traction device 1. FIG. 5 is a right side view of the maxillary traction device 1. FIG. 6 is an enlarged side view of the area defined by the dash-dot lines in FIG. 5 of the maxillary traction device 1.

The mouthpiece 10 is attached to a maxilla inside a mouth of a human body. In this embodiment, a maxilla inside a mouth includes a hard palate, a soft palate, and teeth. The traction device 20 is attached to the head of the human body. The traction device 20 comes into contact with areas of the face FC of the human body to pull the mouthpiece 10 in the anterior direction of the human body from a position in front of the face FC and detached from the face FC.

Figure 7:
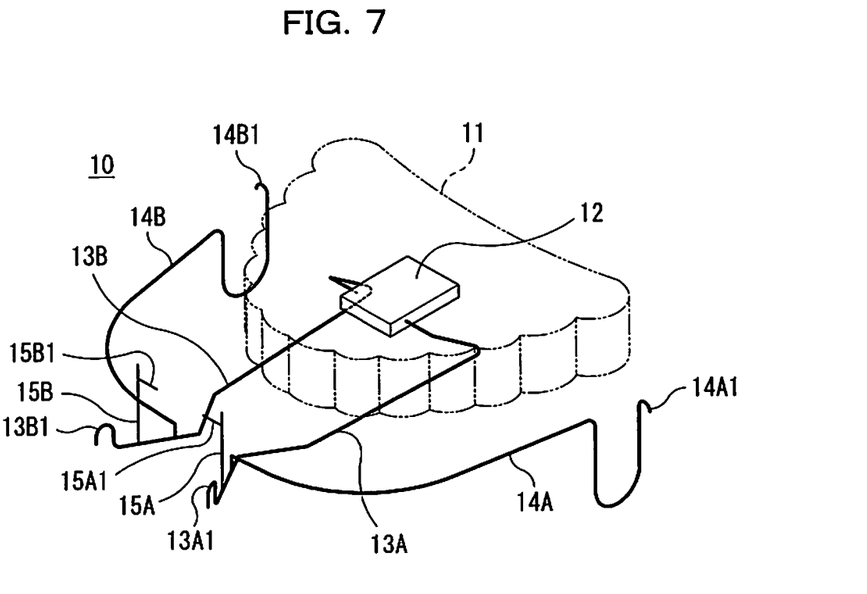
FIG. 7 is a forward perspective view of a mouthpiece according to a first embodiment.
Figure 8:
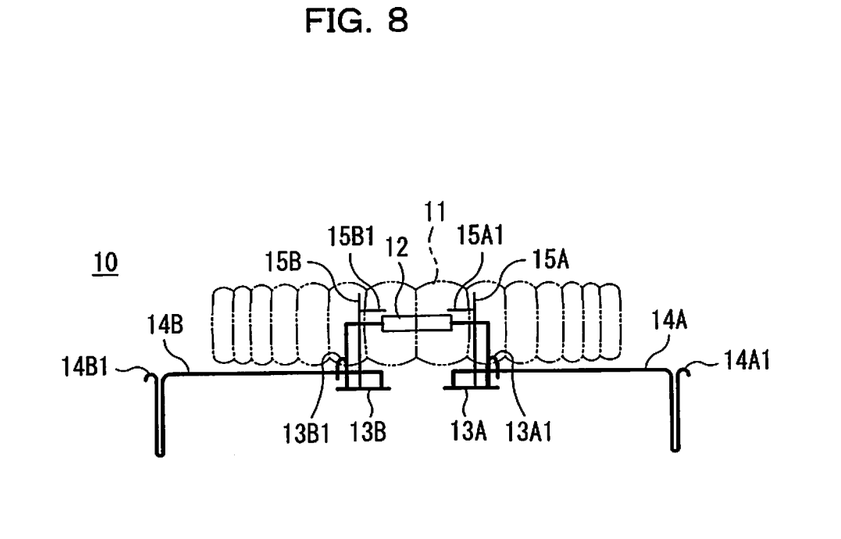
FIG. 8 is a front view of a mouthpiece according to a first embodiment.
Figure 9:
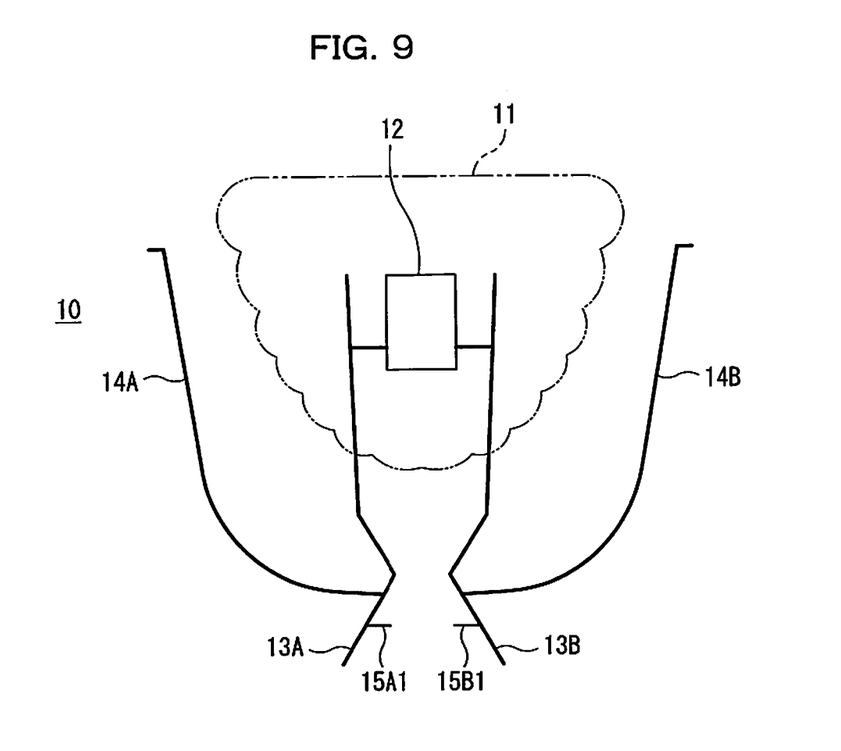
FIG. 9 is a bottom view of a mouthpiece according to a first embodiment.

As illustrated in FIGS. 7 to 10, the mouthpiece 10 includes a maxillary contact 11, an adjustment mechanism 12, a pair of forward extensions 13A and 13B, a pair of curved members 14A and 14B, and a pair of upward extensions 15A and 15B. FIG. 7 is a forward perspective view of the mouthpiece 10. FIG. 8 is a front view of the mouthpiece 10. FIG. 9 is a bottom view of the mouthpiece 10.

In this embodiment, the forward extensions 13A and 13B, the curved members 14A and 14B, and the upward extensions 15A and 15B are thin wire components. For example, these components may be prepared by the deformation of a columnar or cylindrical material. Alternatively, these components may be molded with metal dice.

The maxillary contact 11 is composed of resin. The maxillary contact 11 comes into contact with the lower surface of the maxilla inside the mouth (oral cavity) of the human body. In this embodiment, the maxillary contact 11 comes into contact with the maxillary teeth from the interior (the posterior side of the human body).

In this embodiment, the adjustment mechanism 12 is configured to deform the outer edge of the maxillary contact 11 so as to increase the distance between the maxillary teeth or to expand the row of maxillary teeth in the lateral direction of the human body. For example, the adjustment mechanism 12 may have the configuration described in Japanese Unexamined Patent Application Publication No. 2009-89928. Alternatively, the adjustment mechanism 12 may have another configuration. The mouthpiece 10 may not include the adjustment mechanism 12.

The paired forward extensions 13A and 13B are bilaterally symmetric. In this specification, "bilaterally symmetric" refers to symmetry with respect to the sagittal plane, which is orthogonal to a lateral direction of the human body and disposed at a center of the human body in the lateral direction. Therefore, the pair of forward extensions 13A and 13B will be described by focusing on the forward extension 13A.

In this embodiment, one end of the forward extension 13A is fixed to the adjustment mechanism 12. The forward extension 13A may be fixed to the maxillary contact 11. With the mouthpiece 10 attached to the maxilla inside the mouth of the human body (mouthpiece attached state), the forward extension 13A extends in the anterior direction of the human body to the exterior of the mouth of the human body. A hook 13A1 is formed on the other end of the forward extension 13A (the end of the forward extension 13A opposite to the end fixed to the adjustment mechanism 12 or the anterior end of the forward extension 13A).

The paired curved members 14A and 14B are bilaterally symmetric. Therefore, the pair of curved members 14A and 14B will be described by focusing on the curved member 14A.

One end of the curved member 14A is fixed to a part of the forward extension 13A on the exterior of the mouth of the human body while the mouthpiece in being attached. The curved member 14A curvedly extends in the posterior direction of the human body to the exterior of the mouth of the human body while the mouthpiece in being attached. A hook 14A1 is formed on the other end of the curved member 14A (the end of the curved member 14A opposite to the end fixed to the forward extension 13A or the posterior end of the curved member 14A).

The paired upward extensions 15A and 15B are bilaterally symmetric. Therefore, the pair of upward extensions 15A and 15B will be described by focusing on the upward extension 15A.

One end of the upward extension 15A is fixed to a part of the forward extension 13A on the exterior of the mouth of the human body while the mouthpiece is being attached. In this embodiment, one end of the upward extension 15A is fixed at a position anterior to the position where the curved member 14A is fixed.

The upward extension 15A extends in the superior direction of the human body to the exterior of the mouth of the human body while the mouthpiece is being attached. A hook 15A1 is formed on the other end of the upward extension 15A (the end of the upward extension 15A opposite to the end fixed to the forward extension 13A or the superior end of the upward extension 15A).

Figure 10:
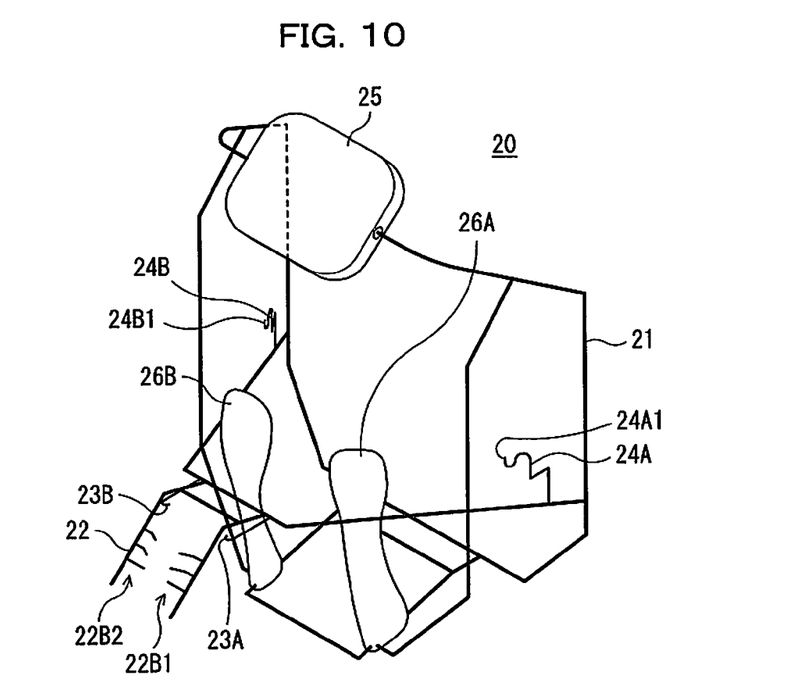
FIG. 10 is a forward perspective view of a traction device according to a first embodiment.
Figure 11:
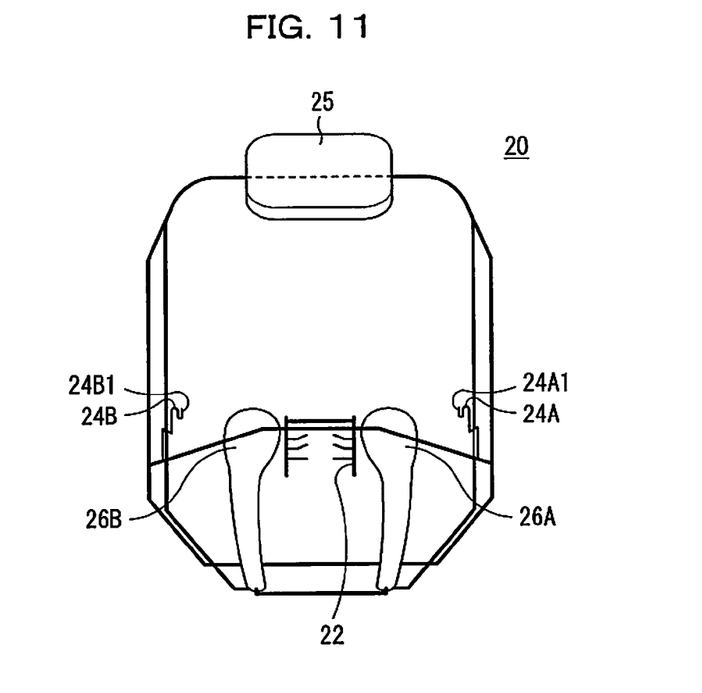
FIG. 11 is a front view of a traction device according to a first embodiment.
Figure 12:
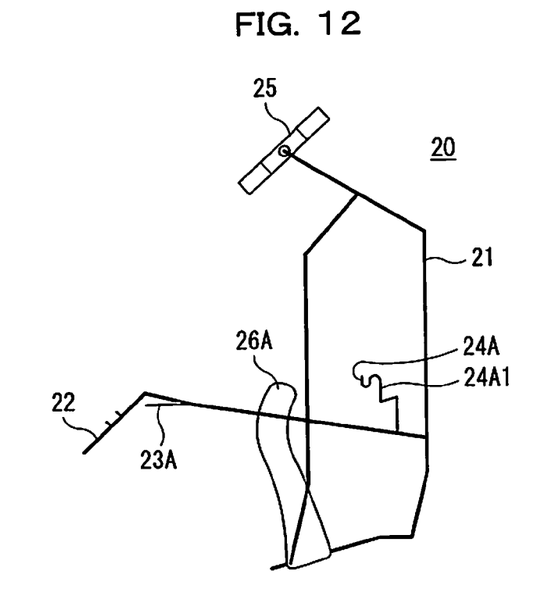
FIG. 12 is a right side view of a traction device according to a first embodiment.

As illustrated in FIGS. 10 to 12, the traction device 20 includes a base 21, a forward engaging piece 22, a pair of upward engaging pieces 23A and 23B, a pair of rotational engaging pieces 24A and 24B, an upper contact body 25, a right lower contact 26A, and a left lower contact 26B.

In this embodiment, the right lower contact 26A and the left lower contact 26B constitute a lower contact body. The base 21, the upper contact body 25, and the lower contact body constitute a support assembly. The forward engaging piece 22, the upward engaging pieces 23A and 23B, and the rotational engaging pieces 24A and 24B constitute an engaging assembly.

FIG. 10 is a forward perspective view of the traction device 20. FIG. 11 is a front view of the traction device 20. FIG. 12 is a right side view of the traction device 20.

In this embodiment, the base 21, the forward engaging piece 22, the upward engaging pieces 23A and 23B, and the rotational engaging pieces 24A and 24B are thin wire components. For example, these components may be prepared by deformation of a columnar or cylindrical material. Alternatively, these components may be molded with metal dice.

With the traction device 20 attached to the head of the human body (traction device attached state), the base 21 includes a part disposed at a position in front of the face FC of the human body and detached from the face FC and a part disposed at a position on the side of the head of the human body and detached from the head. In this embodiment, the traction device 20 is attached to the head of the human body with a fixing strip FB extending so as to surround the base 21. The fixing strip FB may be fixed to the base 21. For example, the fixing strap FB is a band, a strap, or a belt.

The forward engaging piece 22 extends in the anterior direction of the human body from a part of the base 21 near the nose and the mouth (i.e., a part disposed at a position in front of the face FC and detached from the face FC) while the traction device is being attached.

The forward engaging piece 22 includes a base section 22A, a tip section 22B, and a forward elastic body 22C. In the drawings, the forward elastic body 22C is indicated by a dotted line to distinguish from other components.

The base section 22A constitutes a part of the forward engaging piece 22 close to the base 21 (base end). The tip section 22B constitutes a part of the forward engaging piece 22 opposite to the base 21 (tip end). The base section 22A extends in a direction along the anterior-posterior direction of the human body while the traction device is being attached. The tip section 22B tilts in the inferior direction of the human body while the traction device is being attached.

The tip section 22B has multiple (three in this embodiment) pairs of hooks 22B1 and 22B2. The hooks 22B1 and 22B2 in each pair are bilaterally symmetric. Three pairs of hooks 22B1 and 22B2 are disposed along the tip section 22B at an equal pitch. Therefore, a pair of hooks 22B1 and 22B2 will be described by focusing on the hook 22B1 of the central pair of hooks 22B1 and 22B2 among the three pairs of hooks 22B1 and 22B2.

The hook 22B1 is disposed at a position anterior to the position of the hook 15A1 with the traction device 20 attached to the head of the human body and the mouthpiece 10 attached to the maxilla inside the mouth of the human body (maxillary traction device attached state).

In this embodiment, the forward elastic body 22C is composed of an annular rubber. The forward elastic body 22C may be an elastic body, such as a spring or a torsion bar. The forward elastic body 22C is stretched between the hook 22B1 and the hook 15A1 while the maxillary traction device is being attached. This causes the forward elastic body 22C to pull the forward extension 13A via the upward extension 15A in the anterior direction of the human body by an elastic force while the maxillary traction device is being attached.

In this way, the forward engaging piece 22 can pull the mouthpiece 10 in the anterior direction of the human body.

The hooks 22B1 and 22B2 between which the forward elastic body 22C is to be stretched are selected among the multiple pairs of hooks 22B1 and 22B2 provided at different positions in accordance with the shape and size of the head and face of the human body to pull the mouthpiece 10 in an appropriate direction.

The paired upward engaging pieces 23A and 23B are bilaterally symmetric. Therefore, the pair of upward engaging pieces 23A and 23B will be described by focusing on the upward engaging piece 23A.

The upward engaging piece 23A extends in the anterior direction of the human body from a part of the base 21 near the nose and the mouth (i.e., a part disposed at a position in front of the face FC and detached from the face FC) while the traction device is being attached.

A hook 23A1 is formed at the tip of the upward engaging piece 23A (the end of the upward engaging piece 23A opposite to the base 21). The hook 23A1 is disposed at a position superior to the position of the hook 13A1 while the maxillary traction device is being attached.

The upward engaging piece 23A has an upward elastic body 23C. In the drawings, the upward elastic body 23C is indicated by a dotted line to distinguish from other components. In this embodiment, the upward elastic body 23C is composed of an annular rubber. The upward elastic body 23C may be an elastic body, such as a spring or a torsion bar.

The upward elastic body 23C is stretched between the hook 23A1 and the hook 13A1 while the maxillary traction device is being attached. This causes the upward elastic body 23C to pull the forward extension 13A in the superior direction of the human body by an elastic force while the maxillary traction device is being attached.

In this way, the upward engaging piece 23A can pull the mouthpiece 10 in the superior direction of the human body.

The paired rotational engaging pieces 24A and 24B are bilaterally symmetric. Therefore, the pair of rotational engaging pieces 24A and 24B will be described by focusing on the rotational engaging piece 24A.

The rotational engaging piece 24A extends in the superior direction of the human body from a part of the base 21 between an ear and the nose when the head of the human body is viewed from the side (i.e., a part detached from the head on the side of the head of the human body) while the traction device is being attached.

A hook 24A1 is formed at the tip of the rotational engaging piece 24A (the end of the rotational engaging piece 24A opposite to the base 21). The hook 24A1 is disposed at a position superior to the position of the hook 14A1 while the maxillary traction device is being attached.

The rotational engaging piece 24A includes a rotational elastic body 24C. In the drawings, the rotational elastic body 24C is indicated by a dotted line to distinguish from other components. In this embodiment, the rotational elastic body 24C is composed of an annular rubber. The rotational elastic body 24C may be any other elastic body.

The rotational elastic body 24C is stretched between the hook 24A1 and the hook 14A1 while the maxillary traction device is being attached. This causes the rotational elastic body 24C to pull the posterior end of the curved member 14A in the superior direction of the human body by an elastic force while the maxillary traction device is being attached.

In this way, the rotational engaging piece 24A can apply a torque that rotates the mouthpiece 10 in a predetermined rotational direction to the mouthpiece 10. The rotational direction indicates a direction in which a posterior end, which is an end of the mouthpiece 10 in a posterior direction of the human body inside the mouth, is moved in a superior direction of the human body and an anterior end, which is an end of the mouthpiece 10 in the anterior direction of the human body inside the mouth, is moved in an inferior direction of the human body. As illustrated in FIG. 6, the rotational direction RD is a counterclockwise direction along a rotational center axis extending in the lateral direction of the human body when the head of the human body is viewed from the right side.

This applies a torque to the maxilla. As a result, the further end (a part on the posterior side) of the maxilla of the human body (user) positioned at a relatively lower portion (for example, the posterior part of the lower surface of the maxilla is disposed at an inferior position) can grow in an appropriate direction.

As described above, the maxillary traction device 1 includes the elastic bodies provided independently for the forward engaging piece 22, the upward engaging pieces 23A and 23B, and the rotational engaging pieces 24A and 24B. These elastic bodies can readily adjust the force pulling the mouthpiece 10 in the anterior direction, the force pulling the mouthpiece 10 in the superior direction, and the intensity of the torque.

The engaging assembly including the forward engaging piece 22, the upward engaging pieces 23A and 23B, and the rotational engaging pieces 24A and 24B can engage with the mouthpiece 10.

The upper contact body 25 is fixed to the base 21 at a part near the forehead (i.e., a part disposed at a position in front of the face FC and detached from the face FC) while the traction device is being attached. The upper contact body 25 comes into contact with the forehead of the face FC while the traction device is being attached. In this embodiment, the upper contact body 25 is flat. The upper contact body 25 may be bent to increase the area to be in contact with the forehead.

The upper contact body 25 is fixed to the base 21 such that the upper contact body 25 is rotatable around a rotational axis extending in a lateral direction of the human body. Thus, the upper contact body 25 reliably comes into contact with the forehead regardless of the variation in the angle to the face FC formed by a part of the face FC in contact with the lower contact body and the forehead. In this way, the maxilla can be readily pulled in an appropriate direction. The upper contact body 25 may be fixed without rotation.

The right lower contact 26A and the left lower contact 26B are bilaterally symmetric. Therefore, the right lower contact 26A and the left lower contact 26B will be described by focusing on the right lower contact 26A.

The right lower contact 26A is fixed to the base 21 at a part below the cheek (i.e., a part disposed at a position in front of the face FC and detached from the face FC) while the traction device is being attached. The right lower contact 26A may be fixed to another part of the base 21.

The right lower contact 26A comes into contact with the face FC on the right side of the sagittal plane while the traction device is being attached. Furthermore, the right lower contact 26A comes into contact with only apart including at least apart of the maxilla or cheek of the face FC (the area between the maxilla and the cheek in this embodiment) while the traction device is being attached.

Such a mechanism can more stably support the engaging assembly without substantial diminishment of the function of the eyes, the nose, and/or the mouth.

The right lower contact 26A may come into contact with only one of the maxilla and the cheek while the traction device 20 is being attached to the head of the human body.

The right lower contact 26A and the left lower contact 26B constitute lower contact body in contact with an area of the face FC below the forehead and above a mandible.

The support assembly including the upper contact body 25 and the lower contact body can support the engaging assembly through contact with the face FC of the human body.

Operation

The operation of the maxillary traction device 1 described above will now be described with reference to FIGS. 2 to 6.

The mouthpiece 10 is attached to the maxilla inside the mouth of the user or human body. The user extends the fixing strip FB to surround the base 21 and attach the traction device 20 to the head.

In this way, the upper contact body 25 comes into contact with the forehead of the face FC. The right lower contact 26A comes into contact with the face FC in an area between the maxilla and the right cheek in the front view of the user (when the user is viewed from the front). The left lower contact 26B comes into contact with the face FC in an area between the maxilla and the left cheek in the front view of the user.

The user stretches the first forward elastic body 22C between the hook 22B1 and the hook 15A1 and the second forward elastic body 22C between the hook 22B2 and the hook 15B1.

The user stretches the first upward elastic body 23C between the hook 23A1 and the hook 13A1 and the second upward elastic body 23C between the hook 23A1 and the hook 13A1. The user stretches the first rotational elastic body 24C between the hook 24A1 and the hook 14A1 and the second rotational elastic body 24C between the hook 24B1 and the hook 14B1.

The order of attachment of the mouthpiece 10 and the traction device 20 and the order of stretching the elastic bodies may be different from those described above. The attachment of the mouthpiece 10 and the traction device 20 and/or the stretching of the elastic bodies may be performed by someone other than the user (such as an assistant).

After the attachment of the maxillary traction device 1 to the user, the forward elastic body 22C pulls the forward extensions 13A and 13B via the upward extensions 15A and 15B in the anterior direction of the user by an elastic force. That is, the traction device 20 pulls the mouthpiece 10 in the anterior direction of the user.

The upward elastic body 23C pulls the forward extensions 13A and 13B in the superior direction of the user by an elastic force. That is, the traction device 20 pulls the mouthpiece 10 in the superior direction of the user.

The rotational elastic body 24C pulls the ends of the curved members 14A and 14B on the posterior side of the user to the superior direction of the user by an elastic force. That is, the traction device 20 applies a torque for rotating the mouthpiece 10 in the rotational direction RD to the mouthpiece 10.

The upper contact body 25, the right lower contact 26A, and the left lower contact 26B of the traction device 20 receive a reaction force (generated in a reaction) to the force of the traction device 20 pulling the mouthpiece 10 through the transmission of the reaction force to the face FC of the user. That is, the upper contact body 25 pushes the forehead of the face FC while the right lower contact 26A and the left lower contact 26B push the areas between the maxilla and the cheeks of the face FC. Thus, the lower edge of the mandible of the face FC is not pushed in the posterior direction of the human body.

As described above, the support assembly of the traction device 20 according to the first embodiment includes the upper contact body 25 in contact with the forehead of the face FC and the lower contact body (the right lower contact 26A and the left lower contact 26B) in contact with an area of the face FC below the forehead and above the mandible.

In this way, a force in the posterior direction of the human body is avoided from being applied to the lower edge of the mandible. As a result, the growth or movement of the mandible in the anterior direction can be appropriately encouraged.

The variation in the distance between an area above the mandible and the forehead due to the traction of the mouthpiece 10 is small in comparison to the variation in the distance between the lower edge of the mandible and the forehead. Also, the variation in the angle to the face FC formed by an area above the mandible and the forehead due to the traction of the mouthpiece 10 is small in comparison to the variation in the angle to the face FC formed by the lower edge of the mandible and the forehead.

Thus, the configuration described above extends the period in which the upper contact body 25 and the lower contacts 26A and 26B are all in contact with the face FC at appropriate positions. That is, the period of traction of the maxilla in an appropriate direction is extended.

The configuration described above can reduce the complexity of the procedure of appropriate encouragement of the growth or movement of the jaw.

The lower contacts 26A and 26B of the traction device 20 according to the first embodiment is configured to be in contact with at least a part of the maxilla or cheek of the face FC.

Such a mechanism can more stably support the engaging assembly without substantial diminishment of the function of the eyes, the nose, and/or the mouth.

The lower contacts 26A and 26B of the traction device 20 according to the first embodiment comprise the right lower contact 26A configured to be in contact with the face FC on a right side of a sagittal plane, and the left lower contact 26B configured be in contact with the face FC on a left side of the sagittal place.

Such a mechanism can more stably support the engaging assembly without substantial diminishment of the function of the eyes, the nose, and/or the mouth.

The engaging assembly of the traction device 20 according to the first embodiment includes rotational engaging pieces to apply torque to the mouthpiece 10 to rotate the mouthpiece 10 in a rotational direction RD in which a posterior end, which is an end of the mouthpiece 10 in the posterior direction of the human body inside the mouth, is moved in a superior direction of the human body and an anterior end, which is an end of the mouthpiece 10 in the anterior direction of the human body inside the mouth, is moved in the inferior direction of the human body.

In this way, a torque can be applied to the maxilla. As a result, the further end (a part on the posterior side) of the maxilla of the user positioned at a relatively lower portion (for example, the posterior part of the lower surface of the maxilla is disposed at an inferior position) can grow in an appropriate direction.

The forward engaging piece 22 of the traction device 20 according to the first embodiment includes the forward elastic body 22C that pulls the forward extensions 13A and 13B of the mouthpiece 10 in the anterior direction of the human body by an elastic force. The rotational engaging pieces 24A and 24B include the rotational elastic bodies 24C that pull the posterior ends of the curved members 14A and 14B of the mouthpiece 10 in the superior direction of the human body by an elastic force.

The elastic bodies 22C and 24C are provided independently for the forward engaging piece 22 and the rotational engaging pieces 24A and 24B. These elastic bodies can readily adjust the anterior pulling force and the intensity of the torque.

The upper contact body 25 of the traction device 20 according to the first embodiment is configured such that the upper contact body 25 is rotatable around a rotational axis extending in a lateral direction of the human body.

Thus, the upper contact body 25 reliably comes into contact with the forehead regardless of the variation in the angle to the face FC formed by parts of the face FC in contact with the lower contacts 26A and 26B and the forehead. In this way, the maxilla can be readily pulled in an appropriate direction.

The traction device 20 according to the first embodiment may be configured such that the distance is adjustable between the upper contact body 25 and lower contacts 26A and 26B. For example, these distances in the traction device 20 may be adjusted by replacing a member constituting a part of the base 21 with another member having a different length.

Thus, the upper contact body 25 and the lower contacts 26A and 26B reliably come into contact with the face FC regardless of a variable distance between a part of the face FC in contact with the upper contact body 25 and parts of the face FC in contact with the lower contacts 26A and 26B. In this way, the maxilla can be readily pulled in an appropriate direction.

All or at least one of the elastic bodies 22C, 23C, and 24C may be fixed to the traction device 20 according to the first embodiment.

The lower contact body of the traction device 20 according to the first embodiment includes two components (the right lower contact 26A and the left lower contact 26B). Alternatively, the traction device 20 may include only one component.

The lower contact body of the traction device 20 according to the first embodiment may include three or more components. In such a case, the lower contact body of the traction device 20 according to the first embodiment may include a mandibular contact body that comes into contact with the mandible, in addition to the right lower contact 26A and the left lower contact 26B. In such a case also, the force of the mandibular contact body pushing the face FC can be reduced compared to a case without the right lower contact 26A and the left lower contact 26B. Thus, the growth or movement of the mandible in the anterior direction can be appropriately encouraged.

The first embodiment discloses the mouthpiece described below.

The mouthpiece that is to be attached to a maxilla inside a mouth of a human body includes a forward extension extending in the anterior direction of the human body to an exterior of the mouth of the human body and a curved member curvedly extending to the exterior of the mouth from a part of the forward extension disposed on the exterior of the mouth of the human body in a posterior direction of the human body.

Second Embodiment

A maxillary traction device according to a second embodiment of the present invention will now be described. The maxillary traction device according to the second embodiment differs from the maxillary traction device according to the first embodiment in that no torque is applied to the maxilla. This difference is now described below. In the second embodiment, components that are identical or very similar to the first embodiment are indicated by the same reference numerals.

Figure 13:
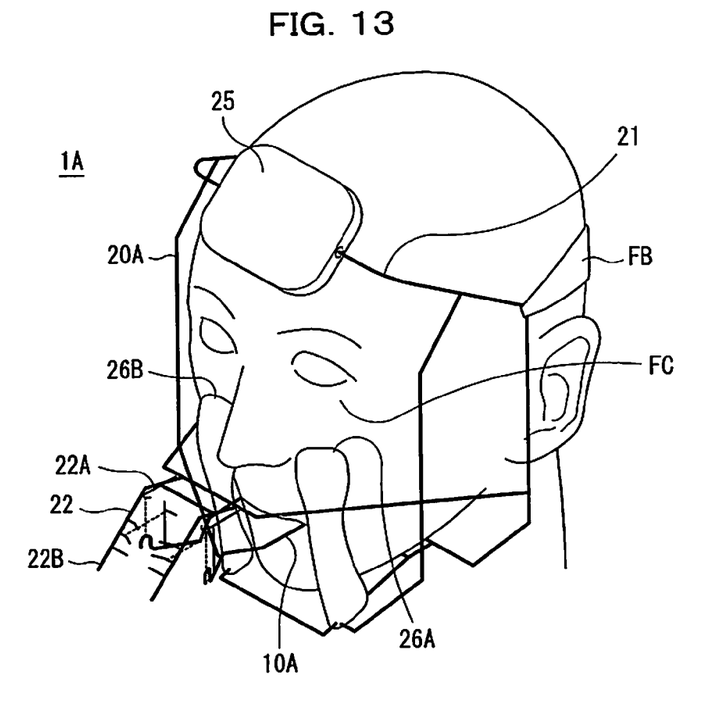
FIG. 13 is a forward perspective view of a maxillary traction device according to a second embodiment.
Figure 14:
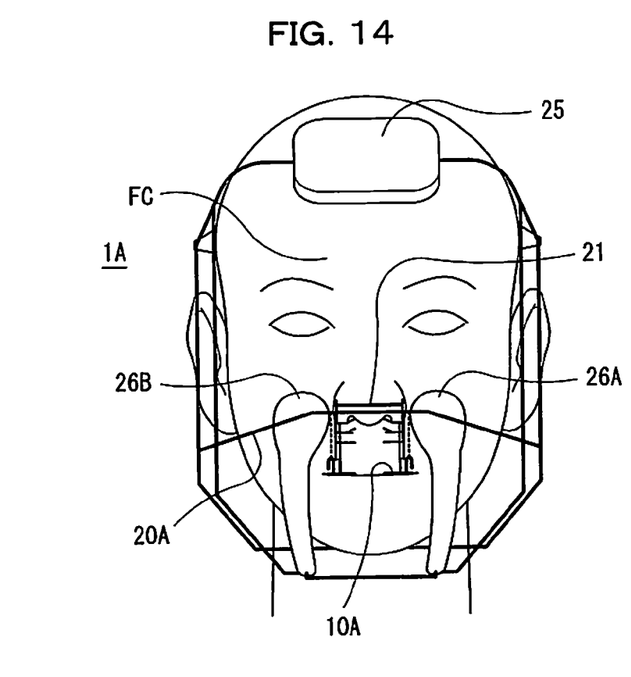
FIG. 14 is a front view of a maxillary traction device according to a second embodiment.
Figure 15:
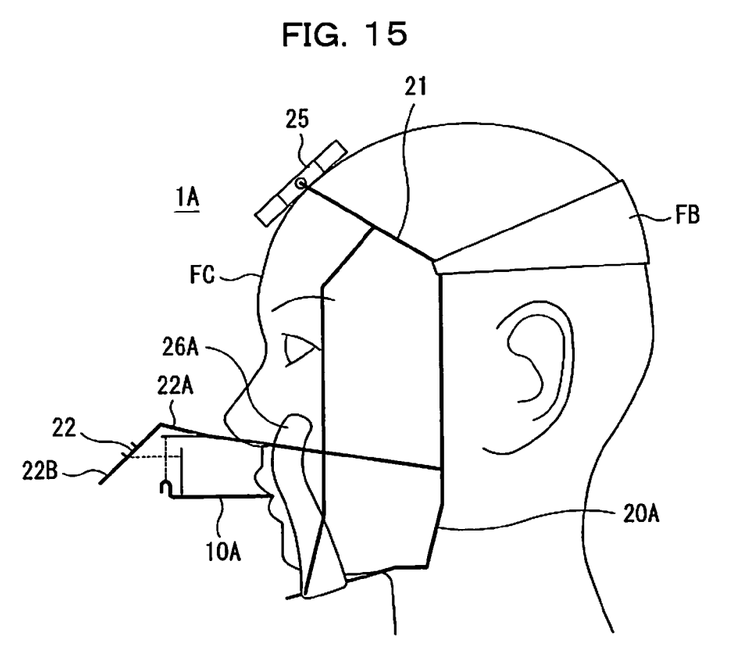
FIG. 15 is a right side view of a maxillary traction device according to a second embodiment.

With reference to FIGS. 13 to 15, a maxillary traction device 1A according to the second embodiment includes a mouthpiece 10A and a traction device 20A. FIG. 13 is a forward perspective view of the maxillary traction device 1A. FIG. 14 is a front view of the maxillary traction device 1A. FIG. 15 is a right side view of the maxillary traction device 1A.

Figure 16:
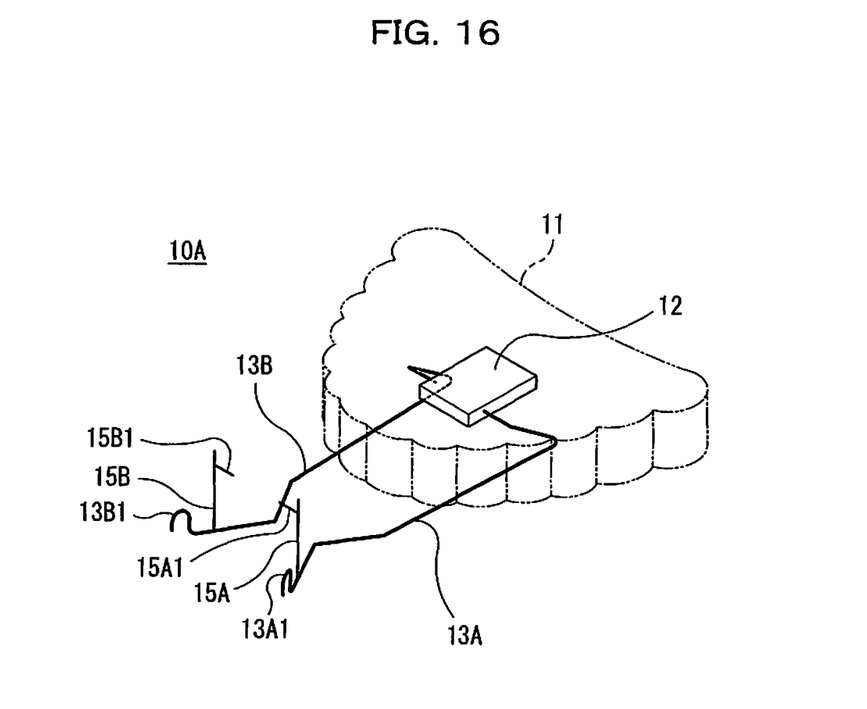
FIG. 16 is a forward perspective view of a mouthpiece according to a second embodiment.
Figure 17:
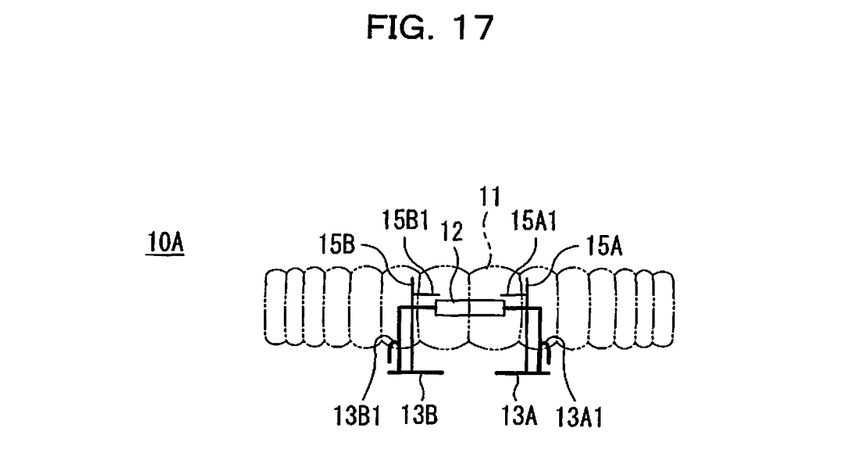
FIG. 17 is a front view of a mouthpiece according to a second embodiment.
Figure 18:
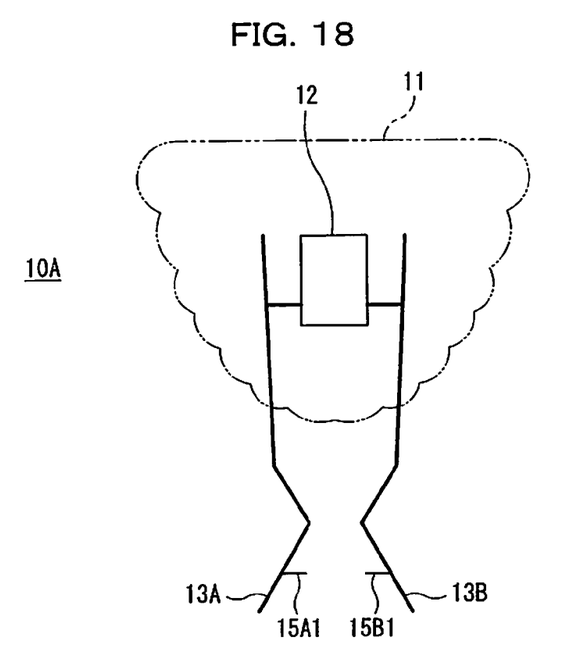
FIG. 18 is a bottom view of a mouthpiece according to a second embodiment.

As illustrated in FIGS. 16 to 18, the mouthpiece 10A has the same configuration as that of the mouthpiece 10 according to the first embodiment except that the curved members 14A and 14B are not provided. FIG. 16 is a forward perspective view of the mouthpiece 10A. FIG. 17 is a front view of the mouthpiece 10A. FIG. 18 is a bottom view of the mouthpiece 10A.

Figure 19:
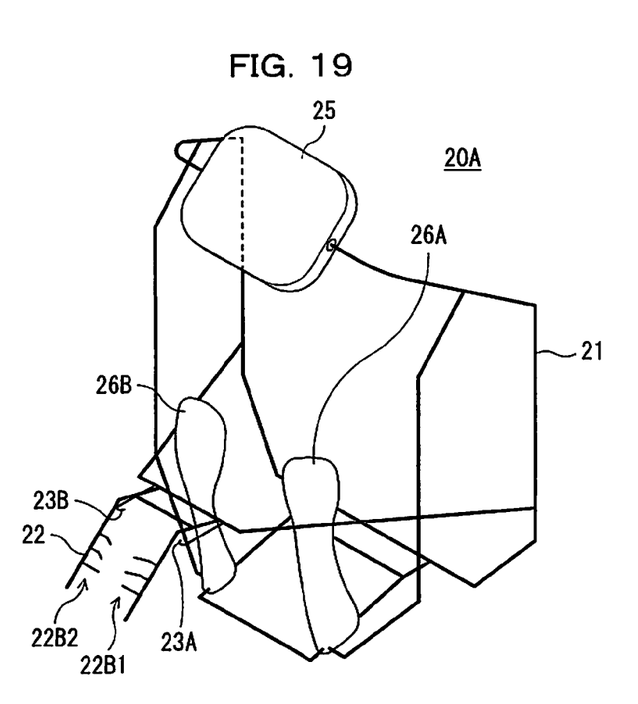
FIG. 19 is a forward perspective view of a traction device according to a second embodiment.
Figure 20:
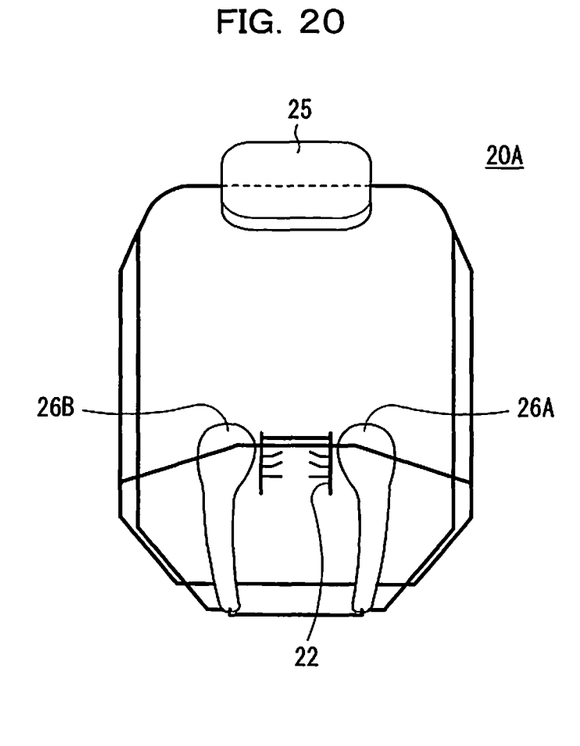
FIG. 20 is a front view of a traction device according to a second embodiment.
Figure 21:
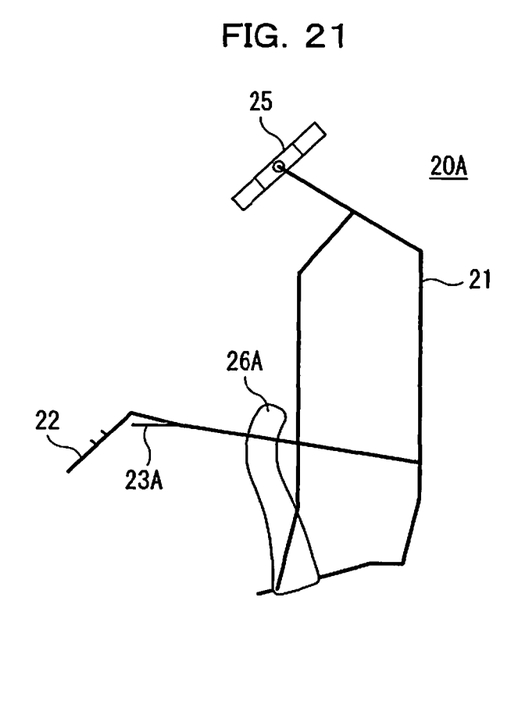
FIG. 21 is a right side view of a traction device according to a second embodiment.

As illustrated in FIGS. 19 to 21, the traction device 20A has the same configuration as that of the traction device 20 according to the first embodiment except that the rotational engaging pieces 24A and 24B and the rotational elastic body 24C are not provided. FIG. 19 is a forward perspective view of the traction device 20A. FIG. 20 is a front view of the traction device 20A. FIG. 21 is a right side view of the traction device 20A.

As described above, the traction device 20A according to the second embodiment achieves the same advantages as those of the traction device 20 according to the first embodiment without the advantage of the application of a torque to the maxilla.

The embodiments of the present invention have been described above. The present invention, however, should not be limited to the embodiments described above. Various modifications comprehensible by one skilled in the art may be made within the scope of the invention.

For example, the examples of the material of the components constituting the maxillary traction device have been described in the embodiments. The maxillary traction device, however, may be composed of materials other than those described as examples.

Various combinations of the embodiments described above and modifications may be employed as other modifications of the embodiments within the scope of the invention.

What is claimed is:

1. A traction device comprising:
  an engaging assembly engaging with a mouthpiece to be attached to a maxilla inside a mouth of a human body; and
  a support assembly supporting the engaging assembly in contact with a face of the human body,
  wherein the engaging assembly pulls the mouthpiece in an anterior direction of the human body,
  the support assembly comprising:
    an upper contact body configured to be in contact with a forehead of the face; and
    a lower contact body configured to be in contact with an area of the face below the forehead and above a mandible,
  the engaging assembly comprising:
    a forward engaging piece to pull the mouthpiece in the anterior direction of the human body; and
    a rotational engaging piece to apply torque to the mouthpiece being pulled in the anterior direction of the human body to rotate the mouthpiece in a rotational direction that moves a posterior end, which is an end of the mouthpiece in a posterior direction of the human body inside the mouth, in a superior direction of the human body and an anterior end, which is an end of the mouthpiece in the anterior direction of the human body inside the mouth, in an inferior direction of the human body.

2. The traction device according to claim 1, wherein the lower contact body is configured to be in contact with at least a part of the maxilla or cheek of the face.

3. The traction device according to claim 2, wherein the lower contact body comprises:
  a right lower contact configured to be in contact with the face on a right side of a sagittal plane; and
  a left lower contact configured to be in contact with the face on a left side of the sagittal place, the sagittal plane being orthogonal to a lateral direction of the human body and disposed at a center of the human body in the lateral direction.

4. The traction device according to claim 3, wherein the right lower contact and the left lower contact are fanned substantially symmetric with respect to the sagittal plane.

5. The traction device according to claim 1, wherein the forward engaging piece comprises:
  a forward elastic body to pull a forward extension of the mouthpiece in the anterior direction by an elastic force, the forward extension extending in the anterior direction of the human body to an exterior of the mouth of the human body, and
  the rotational engaging piece comprises:
    a rotational elastic body to pull a posterior end, which is an end of a curved member in the posterior direction of the human body, in the superior direction of the human body by an elastic force, the curved member curvedly extending outside the mouth from a part of the forward extension of the mouthpiece disposed outside the mouth in the posterior direction of the human body.

6. The traction device according to claim 2, wherein the forward engaging piece comprises:
  a forward elastic body to pull a forward extension of the mouthpiece in the anterior direction by an elastic force, the forward extension extending in the anterior direction of the human body to an exterior of the mouth of the human body, and
  the rotational engaging piece comprises:
    a rotational elastic body to pull a posterior end, which is an end of a curved member in the posterior direction of the human body, in the superior direction of the human body by an elastic force, the curved member curvedly extending outside the mouth from a part of the forward extension of the mouthpiece disposed outside the mouth in th9 posterior direction of the human body.

7. The traction device according to claim 3, wherein the forward engaging piece comprises:
  a forward elastic body to pull a forward extension of the mouthpiece in the anterior direction by an elastic force, the forward extension extending in the anterior direction of the human body to an exterior of the mouth of the human body, and
  the rotational engaging piece comprises:
    a rotational elastic body to pull a posterior end, which is an end of a curved member in the posterior direction of the human body, in the superior direction of the human body by an elastic force, the curved member curvedly extending outside the mouth from a part of the forward extension of the mouthpiece disposed outside the mouth in the posterior direction of the human body.

8. The traction device according to claim 4, wherein the forward engaging piece comprises:
  a forward elastic body to pull a forward extension of the mouthpiece in the anterior direction by an elastic force, the forward extension extending in the anterior direction of the human body to an exterior of the mouth of the human body, and
  the rotational engaging piece comprises:
    a rotational elastic body to pull a posterior end, which is an end of a curved member in the posterior direction of the human body, in the superior direction of the human body by an elastic force, the curved member curvedly extending outside the mouth from a part of the forward extension of the mouthpiece disposed outside the mouth in the posterior direction of the human body.

9. The traction device according to claim 1, wherein the upper contact body is pivotable around a rotational axis extending in a lateral direction of the human body.

10. The traction device according to claim 1, wherein a distance between the upper contact body and the lower contact body is adjustable.

11. A maxillary traction device comprising:
  a mouthpiece to be attached to a maxilla inside a mouth of a human body; and
  a traction device comprising an engaging assembly engaging with the mouthpiece and a support assembly supporting the engaging assembly in contact with a face of the human body, the engaging assembly to pull the mouthpiece in an anterior direction of the human body, the support assembly comprising:
- an upper contact body configured to be in contact with a forehead of the face; and
- a lower contact body configured to be in contact with an area of the face below the forehead and above a mandible, the mouthpiece comprising:
- a forward extension extending in the anterior direction of the human body to an exterior of the mouth of the human body; and
- a curved member curvedly extending outside the mouth from a part of the forward extension disposed outside the mouth of the human body in a posterior direction of the human body, the traction device comprising:
- a forward elastic body to pull the forward extension in the anterior direction of the human body by an elastic force; and
- a rotational elastic body to pull a first posterior end, which is an end of the curved member in the posterior direction of the human body, in a superior direction of the human body by an elastic force so as to apply torque to the mouthpiece being pulled in the anterior direction of the human body to rotate the mouthpiece in a rotational direction that moves a second posterior end, which is an end of the mouthpiece in the posterior direction of the human body inside the mouth, in the superior direction of the human body and an anterior end, which is an end of the mouthpiece in the anterior direction of the human body inside the mouth, in an inferior direction of the human body.

* * * * *